United States Patent [19]

Becker et al.

[11] 4,308,204
[45] Dec. 29, 1981

[54] PROCESS FOR PREPARING THE THIRD COMPONENT OF THE COMPLEMENT FROM HUMAN BLOOD PLASMA

[75] Inventors: Udo Becker, Munich; Norbert Heimburger, Marburg, both of Fed. Rep. of Germany

[73] Assignee: Behringwerke Aktiengesellschaft, Marburg, Fed. Rep. of Germany

[21] Appl. No.: 177,884

[22] Filed: Aug. 14, 1980

[30] Foreign Application Priority Data

Aug. 16, 1979 [DE] Fed. Rep. of Germany ....... 2933015

[51] Int. Cl.³ .............................................. C07G 7/00
[52] U.S. Cl. ................................ 260/112 B; 210/656; 435/226; 435/815
[58] Field of Search .................... 260/112 B; 210/635, 210/645, 656; 435/815, 226, 212

[56] References Cited

U.S. PATENT DOCUMENTS

| | | | |
|---|---|---|---|
| 3,763,137 | 10/1973 | Huber | 260/112 B |
| 3,808,124 | 4/1974 | Dziobkowski | 210/635 |
| 3,943,245 | 3/1976 | Silverstein | 260/112 B |
| 4,022,758 | 5/1977 | Andersson | 260/112 B |
| 4,175,182 | 11/1979 | Schmer | 536/21 |

OTHER PUBLICATIONS

Moore, Transfusion, vol. 16 (3), Philadelphia, 1976, 200–208.

"An Improved Purification Procedure for the Third Component of Complement and BIH Globulin from Human Serum", Molecular Immunology, vol. 16, pp. 767–776, 1979 (Great Britain).

"The Role of Membrane for C3b and C3d in Phagocytosis" Ehlenberger, The Journal of Experimental Medicine, vol. 145, 1977, pp. 357–371.

*Primary Examiner*—Ernest G. Therkorn
*Attorney, Agent, or Firm*—Curtis, Morris & Safford

[57] ABSTRACT

What is disclosed is a process for isolating or purifying the third component of complement (C 3) from blood plasma and other solutions containing C 3 using a material with affinity for C 3 such as protamine or a salt thereof, which is fixed to a carrier.

6 Claims, No Drawings

PROCESS FOR PREPARING THE THIRD COMPONENT OF THE COMPLEMENT FROM HUMAN BLOOD PLASMA

The present invention relates to a process for isolating or purifying of the third component of the complement (C 3) from blood plasma and other solutions containing C 3.

The complement system is part of the immunologic defence system of the body against foreign substances. The immunologic defence is mobilized when foreign substances, for example viruses or bacteria, penetrate into the body, and as a result thereof the complement system is activated, too. The complement system consists substantially of nine components, designated by C 1 to C 9, which are all proteins. C 3, which is present in normal blood plasma in an amount of about 120 mg/dl, plays a central part. C 3 undergoes an enzymatic cleavage by a complex consisting of C 2 and C 4, in the course of the complement activation. The fragment C 3b thus obtained is fixed on the foreign cell to combat it and induces destruction of the cellular membrane by the complement components C 5 to C 9.

A congenital deficiency of C 3 is very rare, whereas pathological processes proceeding with consumption of C 3 occur very often [cf. A. B. Laurell: Komplementfaktoren in der Labormedizin, Laboratoriumsblätter 27, 86-98 (1977)]. These pathological states substantially include all types of acute and chronic bacterial infections, for example streptococcal infections, E. coli and meningococcal sepsis. Moreover a great variety of inflammatory rheumatic diseases as well as autoimmuno diseases of the type lupus erythematodes or immunohemolytic anemia proceed with consumption of C 3.

The determination of C 3 is hence of great importance in diagnostic procedures. A use of C 3 in therapy at the present time is, however, inconceivable, inter alia as an economic process for obtaining C 3 is lacking. The preparatory methods hitherto known according to the state of the art are extremely laborious and include several precipitation, chromatography and electrophoresis steps [cf. H. J. Müller-Eberhard, Methods in Immunology and Immunochemistry, vol. IV, pages 212-217 (1977)]. These methods provide C 3 in a yield of at most 10%.

It has now surprisingly been found that C 3 can be enriched by a very simple process, based on affinity chromatography.

A feature of the present invention therefore is a process for isolating or enriching the third component of the complement C 3 from solutions thereof, which comprises contacting said solution with a material having an affinity for C 3 and which is fixed to a water-insoluble carrier, separating said material from said solution and detaching C 3 from said material.

Protamine, preferably as a salt, more preferably as protamine sulfate, are the preferred substances with affinity for C 3. Salmine sulfate, which is the protamine sulfate from salmon, has also proved advantageous for the purposes of the present invention.

Suitable carrier materials which are practically insoluble in aqueous systems are particular substances such as are conventionally used in affinity chromatography, such as cellulose, Sephadex ®, polyacrylamide and ion exchangers based on these three substances.

Agarose is preferably used. The protamine is fixed to these carrier substances according to known methods. The resulting adsorbent is ready for use in affinity chromatography of C 3, either in form of a column tower packing or in the so-called batch process for the adsorption of C 3.

C 3 is adsorbed from an aqueous solution thereof, preferably from blood plasma, under the following conditions.

The C 3-containing solution, preferably fresh human citrate plasma having a content of C 3 of about 120 mg/dl, is diluted to such a degree that C 3 is adsorbed to the material with affinity for C 3. Dilution is effected preferably with diluted water until a conductivity corresponding approximately to that of a semiphysiological saline solution is reached. The resulting solution is run over a column charged with a material with affinity for C 3, preferably with protamine fixed to a sepharose carrier, which has been equilibrated with semiphysiological saline solution.

The adsorption, washing and elution steps can alternatively be carried out in a batch process. Preferably the adsorption can take place in a batch process, followed by elution in the column. The batch process is advisable especially for large-scale manufacture and elution in the column is advisable especially for the preparation of a material of high purity because elution in the column can be carried out with a buffer gradient which ensures that the required elution conditions can be maintained.

When the column elution process is used, the outlet of the chromatography tube is connected with the flow bulb of an automatically recording photometer and the optical density of the eluate at 280 nm is measured. When the optical density has again reached its base-line, after application of the substance, the protamine sepharose, by way of example, is washed with saline solution, first in the form of a semiphysiological NaCl and subsequently in the form of a physiological NaCl solution, until the optical density has again reached its base-line.

Elution is carried out with aqueous salt solutions with ionic strengths corresponding to that of NaCl solutions of 0.3 to 0.5 ml/l. If a therapeutic administration of the C 3 concentrate is intended, this concentrate is suitably obtained by elution in a batch process using a buffer of $\geq 0.38$ mol of NaCl/l.

The fraction that contains C 3 is recovered. The C 3 assay is run by conventional methods, preferably by an immunological assay using a specific anti C 3 serum.

A C 3 antigen of high purity, for example for immunization purposes, is suitably prepared by elution in a column, using a linear buffer gradient prepared from equal parts by volume of saline solution of different concentration, for example a 0.9% physiological saline solution and a 0.5 molar saline solution. The fraction obtained in chromatography may be characterized by polyacrylamide -gel-electrophoresis according to Zwisler, O. and H. Biel [Z. klin. chem. 4, 58 (1966)] prior to pooling them. Experience has shown that the fraction having the higest degree of purity is obtained in that eluate that can be desorbed with 0.38 mol/l of NaCl. The fractions that have the highest degree of purity are combined, concentrated, depending on the intended use, dialyzed and optionally lyophilized. According to examinations with specific antisera, these fractions contain C 3 in a highly purified and native form.

Yields up to 90% can be obtained by the above-described method in one single process step. The yield depends on the desired degree of purity, this degree ranging from 50 to 80%. If desired, the process of the invention may be repeated and/or be combined with other processes applied in protein chemistry with the aim to obtain C 3 in pure form.

It is known that C 3 is a labile protein which is readily degraded to yield the fragments C 3a and C 3b, the latter being degraded to provide C 3c and C 3d. The degree of degradation may be determined by two dimensional immunoelectrophoresis. The C 3 recovered according to the present invention is present in a native, non-degraded state, according to this determination method.

The invention is illustrated by the following example:

EXAMPLE (a) Preparation of the specific adsorbent:

Agarose (Sepharose 4 B manufactured by Messrs. Pharmacia Fine Chemicals of Uppsala, Sweden) is activated with bromocyanogen according to the procedure of Axen, Porath and Ernback [Nature 214, 1302–1304 (1967)].

A quantity of the activated agarose corresponding to a dry weight of 8 g is suspended in 250 ml of 0.1 molar $NaHCO_3$ solution of pH 9 and 0.8 g of salmine sulfate (of Messrs. Roth of Karlsruhe, West Germany) dissolved in 50 ml of the same solution is added while stirring. The resulting mixture is incubated while agitating at room temperature for 16 hours and the resulting gel is subsequently washed with water and with acidic and basic buffers. Prior to use, equilibration is carried out with physiological saline solution diluted at a ratio of 1:2.

(b) Enrichment or obtention of C 3

A glass column of 2.5×22 cm dimensions is charged with agarose that has been loaded with salmine sulfate and equilibrated with physiological saline solution diluted at a ratio of 1:2. 20 ml of human blood plasma anticoagulated with citrate, ACD-solution of EDTA are diluted with distilled water to twice their volume and the product is fed to the column. The light absorption of the eluate leaving the column is measured continuously at 280 nm by a photometer which is connected with a recorder. Proteins without affinity to adsorbent are washed off with 200 ml of the semiconcentrated physiological saline solution and then with 200 ml of physiological saline solution. Afterwards a linear gradient consisting of 200 ml of physiological saline solution and 0.5 molar saline solution, respectively, is applied, and the eluate is collected in 5 ml fractions. Four protein fractions having their light absorption maximum at a ionic strength of 0.30, 0.38, 0.45 and 0.5 are traced by the recorder (Cf. FIG. 1). According to the immunological analysis, the fraction having its peak at 0.38 represents C 3. The fraction is collected and analyzed.

Quantitative immunoloelectrophoresis according to Laurell, C.-B. Analyt. Biochem. 15, 45 (1966) indicates a yield of 89%.

In order to determine the degree of purity, the fractions having their peak at the indicated ionic strength, are analyzed by polyacrylamide-gel-electrophoresis according to Zwisler, O. and H. Biel, Z. klin. chem. 4, 58 (1966) (cf. FIG. 2). C 3 appears as a uniform product; the accompanying impurifying proteins original from the adjacent fractions. If desired, these proteins can be separated from C 3 under the said conditions by repeating the gradient chromatography on salmine agarose.

What is claimed is:

1. A method for isolating or enriching the third component of the complement, C3, from a solution containing C3, which method comprises contacting said solution with a member selected from the group consisting of protamine and salts thereof fixed to a water-insoluble carrier, separating said carrier from said solution, and desorbing C3 from said protamine or salt thereof.

2. A method as in claim 1 wherein said water-insoluble carrier is agarose.

3. A method as in claim 1 wherein said member is protamine.

4. A method as in claim 1 wherein said member is a protamine salt.

5. A method as in claim 4 wherein said protamine salt is protamine sulfate.

6. A method as in claim 5 wherein said protamine sulfate is salmine sulfate.

* * * * *